United States Patent [19]

Rosseels et al.

[11] 4,400,387
[45] Aug. 23, 1983

[54] INDOLIZINE DERIVATIVES AND USES IN THERAPEUTICS

[75] Inventors: Gilbert Rosseels, Relegem; Pierre Nokin, Brussels, both of Belgium

[73] Assignee: S. A. Labaz-Sanofi N.V., Paris, France

[21] Appl. No.: 164,838

[22] Filed: Jun. 30, 1980

[30] Foreign Application Priority Data

Jul. 6, 1979 [GB] United Kingdom ............... 7923599

[51] Int. Cl.³ .................. A61K 31/435; C07D 471/04
[52] U.S. Cl. ..................................... 424/263; 546/112
[58] Field of Search ......................... 546/112; 424/263

[56] References Cited

U.S. PATENT DOCUMENTS 4,103,012  7/1978  Gubin et al. ...................... 544/127

FOREIGN PATENT DOCUMENTS 2707048  9/1977  Fed. Rep. of Germany .
430639  2/1978  U.S.S.R. .

Primary Examiner—Henry R. Jiles
Assistant Examiner—Natalia Harkaway
Attorney, Agent, or Firm—Mason, Kolehmainen, Rathburn & Wyss

[57] ABSTRACT

Indolizine derivatives represented by the general formula:

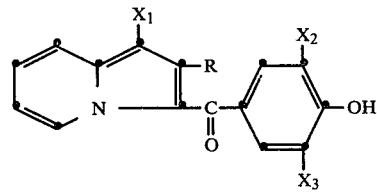

wherein R represents a straight- or branched-chain alkyl radical having from 1 to 8 carbon atoms, or a phenyl group non-substituted or bearing one or two substituents, which may be the same or different, selected from halogen atoms, for example fluorine, chlorine and bromine and from lower alkyl and alkoxy groups, for example methyl and methoxy and $X_1$, $X_2$ and $X_3$, which may be the same or different, each represent hydrogen, chlorine, bromine or methoxy with the proviso that when they are identical $X_1$, $X_2$ and $X_3$ are not simultaneously hydrogen.

They possess an inhibitory activity with respect to the action of xanthine oxidase and of adenosine deaminase as well as an uricosuric action and can be used in the treatment of physiological disturbances consequent upon an excess of uric acid, upon disorders of the immunization system and as antiparasitic agents.

9 Claims, 4 Drawing Figures

HERPETIC NECROSISES     MORTALITY

HERPETIC NECROSISES     MORTALITY

INDOLIZINE DERIVATIVES AND USES IN THERAPEUTICS

This invention relates to heterocyclic compounds and is concerned with novel indolizine derivatives and with a method of preparing the said novel derivatives.

The indolizine derivatives with which the present invention is concerned are the compounds represented by the general formula:

wherein R represents a straight- or branched-chain alkyl radical having from 1 to 8 carbon atoms, or a phenyl group non-substituted or bearing one or two substituents, which may be the same or different, selected from halogen atoms, for example fluorine, chlorine and bromine and from lower alkyl and alkoxy groups, for example methyl and methoxy and $X_1$, $X_2$ and $X_3$, which may be the same or different, each represent hydrogen, chlorine, bromine or methoxy with the proviso that when they are identical $X_1$, $X_2$ and $X_3$ are not simultaneously hydrogen.

A class of compounds falling within the scope of formula I is constituted by those compounds wherein R represents a straight- or branched-chain alkyl radical having from 1 to 8 carbon atoms, a phenyl radical, a monofluoro-, mono-chloro-, mono-bromo-, mono-methyl- or mono-methoxy-phenyl radical, a di-fluoro, di-chloro-, di-bromo-phenyl radical or a methylphenyl radical substituted in the aromatic moiety by an atom of fluorine, chlorine or bromine and $X_1$, $X_2$ and $X_3$, which may be the same or different, each represent hydrogen, chlorine, bromine or methoxy with the proviso that when they are identical, $X_1$, $X_2$ and $X_3$ are not simultaneously hydrogen.

The indolizine derivatives of the invention have been found to possess useful pharmacological properties and more particularly an inhibitory activity with respect to the action of xanthine oxidase and of adenosine deaminase as well as an uricosuric action. Moreover, compounds of the invention have been found to potentiate the cardiovascular effects of the catecholamines.

Another object of the present invention is to provide indolizine derivatives of formula I for use in the treatment of physiological disturbances consequent upon an excess of uric acid and upon disorders of the immunization system.

As examples of physiological disturbances consequent upon an excess of uric acid, gout or tophaceous gout may be cited.

With regard to physiological disturbances consequent upon disorders of the immunization system which may be treated with compounds of the invention, the prevention of the rejection phenomenon in organ transplantations can be cited.

In accordance with another aspect of the invention, there are provided indolizine derivatives of formula I for use in cardiovascular disorders which can be treated by potentiating the cardiovascular effects of the catecholamines, for instance in disturbances of the cerebral vascular system and in cardiac insufficiency.

The present invention is also concerned with pharmaceutical or veterinary compositions containing, as active principle, at least one indolizine derivative of formula I in association with a pharmaceutical carrier or excipient.

The present invention also relates to a process for preparing pharmaceutical or veterinary compositions whereby at least one indolizine derivative of formula I is associated with a pharmaceutical carrier or excipient.

Yet another object of the present invention is to provide a method of treating physiological disturbances consequent upon an excess of uric acid and consequent upon disorders of the immunization system in a host in need of such treatment, method which comprises the administration to said host of an effective dose of at least one indolizine derivative of the invention.

In the treatment of physiological disturbances consequent upon an excess or uric acid such an effective dose can be, for instance, 300 mg daily to a human being weighing about 60 kgs.

In accordance with another aspect of the invention there is provided a method of potentiating the cardiovascular effects of the catecholamines in a host in need thereof, method which comprises the administration to said host of an effective dose of at least one indolizine derivative of the invention.

The compounds of formula I can be prepared following different procedures according to their chemical structure.

Hence, the compounds of the invention can be prepared as follows:

(A) When $X_1$ represents hydrogen or methoxy, $X_2$ is chlorine, bromine or methoxy and $X_3$ is hydrogen, by condensing in a suitable solvent such as dichloroethane, a 2-alkyl- or 2-aryl-indolizine of the general formula:

in which $X_1$ represents hydrogen or methoxy and R has the same meaning as given above, with a benzoic acid chloride derivative of general formula:

in which $X_2$ represents chlorine, bromine or methoxy and Ts represents a p-toluenesulphonyl radical to obtain an indolizine derivative of general formula:

IV in which $X_1$ represents hydrogen or methoxy, $X_2$ represents chlorine, bromine or methoxy and Ts has the same meaning as given above, which is refluxed with an alkali metal hydroxide for example sodium hydroxide so as to provide the corresponding metal salt which is subsequently hydrolysed at room-temperature in the presence of a hydrohalic acid, for example hydrochloric acid, to obtain the required compound of formula I.

The condensation will be carried out at room-temperature or by gently heating the reaction medium to about 50° C.

(B) When $X_1$ represents hydrogen or methoxy and $X_2$ and $X_3$, which are the same or different, each represent chlorine, bromine or methoxy, by condensing at room-temperature in a suitable solvent such as dichloroethane a 2-alkyl- or 2-aryl-indolizine of general formula II with a p-hydroxybenzoic acid chloride derivative of the general formula:

V in which $X_2$ and $X_3$, which are the same or different, represent chlorine, bromine or methoxy, to obtain the required compound of formula I.

(C) When $X_1$ represents bromine and $X_2$ and $X_3$, which are the same or different, each represent hydrogen, chlorine, bromine or methoxy by reacting bromine with a benzoyl-indolizine derivative of the general formula:

VI in which R has the same meaning as given above and $X_2$ and $X_3$, which are the same or different, each represent hydrogen, chlorine, bromine or methoxy, the reaction taking place at room-temperature in a suitable solvent such as dioxan and in the presence of an alkali metal acetate, for example sodium acetate, to obtain the required compound of formula I.

As another suitable solvent, acetic acid can be cited. However, this solvent will only be used when the starting compound represented by formula VI is mono-substituted in the benzoyl moiety by chlorine, bromine or methoxy.

The aforesaid process can be performed by placing in contact one molar equivalent of a compound of formula VI with one, two or three molar equivalents of bromine. Thus, it has been observed that:

when one molar equivalent of bromine is used, the halogenation is selectively achieved in the 1-position of the indolizine ring of the benzoyl-indolizine derivative of formula VI, this compound of formula VI being unsubstituted, monosubstituted or disubstituted by chlorine, bromine or methoxy in the benzoyl moiety.

when two molar equivalents of bromine are used, halogenation occurs not only in the 1-position of the indolizine ring of the compound of formula VI but also in the 3- and 5-positions of the benzoyl moiety. For this reason, the aforesaid process will preferably be carried out starting from a compound of formula VI bearing a chlorine or bromine atom or a methoxy group in the benzoyl moiety so as to avoid mixtures of halogenated compounds.

It is evident that, when one molar equivalent of a 2-substituted-3-(3-chloro-, 3-bromo- or 3-methoxy-4-hydroxy-benzoyl)-indolizine of formula VI is used with two molar equivalents of bromine, separation of the mixture of halogeno-derivatives so obtained is necessary. This separation can be achieved by conventional methods, for example by chromatography on a column.

when three molar equivalents of bromine are used together with one molar equivalent of 2-substituted-3-(4-hydroxy-benzoyl)-indolizine of formula VI the corresponding tri-halogeno-derivative of formula I is obtained in a selective manner.

(D) When $X_1$ represents chlorine and $X_2$ and $X_3$, which are the same or different, each represent hydrogen, chlorine, bromine or methoxy by reacting N-chlorosuccinimide with a benzoyl-indolizine derivative of the general formula:

VII in which R and Ts have the same meaning as given above and $X_2$ and $X_3$, which are the same or different, each represent hydrogen, chlorine, bromine or methoxy, the reaction taking place in a suitable solvent such as dichloroethane and between 0° C. and room-temperature, to obtain an indolizine derivative of the general formula:

VIII in which R, Ts, $X_2$ and $X_3$ have the same meaning as in formula VII, which is refluxed with an alkali metal hydroxide, for example sodium hydroxide, so as to provide the corresponding alkali metal salt which is subsequently hydolysed in the presence of a hydrohalic acid, for example hydrochloric acid, to obtain the required compound of formula I.

The aforesaid process will be performed by placing in contact one molar equivalent of a compound of formula VII with one molar equivalent of N-chlorosuccinimide, this imide being preferably used in a slight excess. When one molar equivalent of a compound of formula VII is reacted with one molar equivalent of N-chlorosuccinimide, the halogenation is selectively achieved in the 1-position of the indolizine ring of the benzoyl indolizine derivative of formula VII, this compound of formula VII being unsubstituted, monosubstituted or disubstituted by chlorine, bromine or methoxy in the benzoyl moiety.

The chemical structure of the compounds prepared in accordance with the above process has been determined by examining the N.M.R. spectrum of the compounds in question. This chemical structure was found to be that of the indolizine derivatives represented by formula I above.

For example, it has been proved that when a 2-substituted-3-(4-hydroxybenzoyl)-indolizine is brominated in accordance with process (C) above so as to obtain the mono-bromo derivative, the bromine atom is attached in the 1-position of the indolizine ring: the characteristics of a p-disubstituted aromatic ring are registered and no singulet is recorded with respect to the $H_1$ proton.

As an example, the N.M.R. data registered with respect to 1-bromo-2-ethyl-3-(4-hydroxy-benzoyl)-indolizine are listed hereunder.

| Chemical shifts (in ppm) | | | | | Couple constants |
|---|---|---|---|---|---|
| $\delta 1$ | $\delta 5$ | $\delta 6$ | $\delta 7$ | $\delta 8$ | (in cps) |
| — | 9.0 dt | 6.91 | 7.23 | 7.56 | $AA' = 7.56$ $J_{6,7} = 6.5$ |
| | | | | | $BB' = 6.90$ $J_{7,8} = 9$ |
| | | | | | $J_{5,6} = 7$ |

(solvent: DMSOd$_6$, referent: TMS i.e. tetramethylsilane)

Similarly, when process (C) is employed using a 2-substituted-3-(3-bromo-4-hydroxy-benzoyl)-indolizine, in order to obtain a dibromo-derivative, the second bromine so introduced in the molecule is located in the 1-position of the indolizine ring: the N.M.R. spectrum shows the presence of a bromine atom in the 1-position of the indolizine (absence of $H_1$ proton) and of a bromine atom in the ortho-position of the hydroxyl radical (the multiplicity and the chemical shift are in agreement with such a structure).

As an example, the N.M.R. data registered with respect to 1-bromo-2-ethyl-3-(3-bromo-4-hydroxy-benzoyl)-indolizine are:

| Chemical shifts (in ppm) | | | | | Couple constants |
|---|---|---|---|---|---|
| $\delta 1$ | $\delta 5$ | $\delta 6$ | $\delta 7$ | $\delta 8$ | (in cps) |
| | | | | $H_C = 7.80$ d | $J_{A,B} = 8.4$ |
| | | | | | $J_{6,7} = 6.75$ |
| — | 9.18 dt | 6.96 m | 7.27 m | 7.54 $H_B = 7.55$ q | $J_{B,C} = 2.0$ |
| | | | | | $J_{5,6} = 7.0$ |
| | | | | $H_A = 7.09$ d | $J_{7,8} = 8.8$ |

(solvent: DMSOd$_6$, referent: TMS)

In the case of the tribromo-derivatives, the presence of a singulet attributed to the p-hydroxy-benzoyl moiety proves that two bromine atoms are in the ortho-position of the hydroxyl radical.

As an example, the N.M.R. data registered with respect to 1-bromo-2-ethyl-3-(3,5-dibromo-4-hydroxybenzoyl)-indolizine are listed hereunder:

| Chemical shifts (in ppm) | | | | | Couple constants |
|---|---|---|---|---|---|
| $\delta 1$ | $\delta 5$ | $\delta 6$ | $\delta 7$ | $\delta 8$ | (in cps) |
| | | | | | $J_{5,6} = 7.0$ |
| — | 9.28 dt | 7.01 m | 7.33 m | 7.77 dt | 7.81 s | $J_{8,7} = 8.75$ |
| | | | | | $J_{5,6} = 6.5$ |

(solvent: DMSOd$_6$, referent: TMS)

The compounds of formula II are either known compounds having been described in British Pat. No. 1,518,443 or compounds which can be prepared by the method described by GUBIN et al, in Eur. J. Med. Chem., 1977, 12, 345.

The compounds of formula III can be obtained by reacting thionyl chloride with 3-chloro-, 3-bromo- or 3-methoxy-4-p-toluenesulphonyl-benzoic acid. These p-toluenesulphonyl derivatives can themselves be obtained by reacting p-toluenesulphonyl chloride and 3-chloro-, 3-bromo- or 3-methoxy-4-hydroxy-benzoic acid. The chloro- and bromo-benzoic acid derivatives in question are known compounds having been described by A. S. HUSSEY et al in J. Am. Chem. Soc. 78, 850 (1950) and in Patent No. 69,116 of the German Democratic Republic while the methoxy-benzoic acid derivative is commercially available.

With respect to the compounds of formula V, these can also be obtained in accordance with known procedures. For instance, 3-bromo-4-hydroxy-5-chloro-benzoyl chloride is obtained by reacting thionyl chloride with 3-bromo-4-hydroxy-5-chloro-benzoic acid, itself prepared from 3-bromo-4-hydroxy-benzoic acid and concentrated hydrochloric acid in the presence of potassium chlorate.

The compounds of formulae VI and VII in which $X_2$ and $X_3$ each are hydrogen are known compounds having been disclosed in the above British Patent while the other compounds of formulae VI and VII are either compounds of the invention or compounds which can be prepared in accordance with processes described above.

Uric acid in man is formed primarily by the xanthine oxidase-catalyzed oxidation of hypoxanthine and xanthine.

Presently, allopurinol is one of the most widely commercialized drugs for the therapy of primary hyperuricemia of gout. In contrast with the uricosuric agents that increase the renal excretion of urate, allopurinol inhibits the terminal steps in uric acid biosynthesis.

At low concentrations, allopurinol, the chemical structure of which is close to that of xanthine and hypoxanthine, is an excellent substrate for and competitive inhibitor of xanthine oxidase. Oxypurinol, the metabolite formed by the action of xanthine oxidase on allopurinol is an extremely powerful non-competitive inhibitor of the same enzyme. Therefore, the inhibitory action in question depends on the kinetics of two reactions i.e. the oxidation of oxypurinol on the one hand and the decomposition of the enzyme-oxypurinol complex on the other.

Inhibition of the penultimate and ultimate steps in uric acid biosynthesis reduces the plasma concentration and urinary excretion of uric acid and increases the plasma concentration and renal excretion of the more soluble oxypurine precursors.

Allopurinol resembles purine bases. Therefore, it can also interfere in a metabolic system of purine bases other than xanthine which can be a source of physiological disturbances.

For this reason, it is preferable that the physician should have at his disposal agents which do not resemble purine bases but which are nevertheless capable, as is allopurinol, of exerting an inhibitory activity with respect to the action of xanthine oxidase and thus slow down uric acid biosynthesis.

Furthermore, allopurinol has a relatively complicated chemical structure which renders it difficult to synthesize. Therefore, it is of paramount importance to find agents capable of inhibiting the action of xanthine oxidase which can be prepared more easily than allopurinol.

The indolizine derivatives of the invention comply with these requirements. In this connection, the following compounds may be cited:

2-Ethyl-3-(3,5-dibromo-4-hydroxy-benzoyl)-indolizine.
1-Bromo-2-n-propyl-3-(3,5-dibromo-4-hydroxy-benzoyl)-indolizine.
2-Isopropyl-3-(3,5-dibromo-4-hydroxy-benzoyl)-indolizine.

Benzofuran derivatives, especially, 3-(3,5-dibromo- and 3,5-diiodo-4-hydroxy-benzoyl)-benzofurans have already been reported as possessing an inhibitory activity with respect to the action of xanthine oxidase [Arch. int. Pharmacodyn., 165, 25 (1967)].

It has now been found, in accordance with the present invention, that it is possible to increase to a considerable degree the inhibitory effect of the aforesaid benzofuran derivatives with respect to the action of xanthine oxidase by replacing the benzofuran moiety by the indolizine ring. It has been observed that this replacement provides a class of new inhibitors of the action of xanthine oxidase i.e. the indolizines of the invention, members of which are ten to twenty times more active than the benzofuran derivatives in question.

Indolizine derivatives which have pharmacological properties are already known. It is reported, for example in Eur. J. Med. Chem. previously cited, that some 3-(4-dialkylaminoalkoxy-benzoyl)-indolizine derivatives possess anti-anginal properties.

However, no inhibitory effect with respect to the action of xanthine oxidase on the part of derivatives belonging to the indolizine series has been reported up to present.

It was, therefore, not possible, from present knowledge, to deduce that the compounds of the invention could exert an inhibitory activity with respect to the action of xanthine oxidase.

As indicated above, the compounds of the invention are also endowed with an inhibitory activity with respect to the action of adenosine deaminase. Tests carried out with benzofuran derivatives of which some are disclosed in the aforesaid publication from Arch. int. Pharmacodyn., have demonstrated that, with respect to the inhibition of adenosine deaminase, the action of these benzofuran derivatives is nil or very weak.

It is known that a total lack of immunity can be related to a genetic deficiency in adenosine deaminase which, consequently, suggests new routes for seeking agents capable of regulating the immunization response.

It seems, in fact, that adenosine and deoxyadenosine (or metabolites thereof such as deoxy-ATP) are directly cytotoxic with respect to lymphocytes and inhibit the proliferation, the differentiation and the maturation of the immunocompetent cells.

Inhibitors of adenosine deaminase, such as 3, 4, 7, 8-tetrahydro-3-$\beta$-D-ribofuranosyl-imidazo[4,5-d][1,3]-diazepin-8-ol i.e. coformycin and 9-erythro-(2-hydroxy-3-nonyl)-adenine i.e. EHNA, are already known which potentiate this cytotoxicity.

Thus, the inhibitors of adenosine deaminase could exert an immunosuppressant activity by increasing the intracellular levels of adenosine, or a metabolite thereof, in the lymphocytes.

Contrary to the immunosuppressors presently used, the inhibitors of adenosine deaminase could exert a specific effect with regard to the immunocompetent cells. Moreover, these inhibitors could be of relatively low toxicity with respect to the other kinds of cells since the biosynthesis of adenosine into inosine catalyzed by adenosine deaminase seems to be a relatively minor route of the metabolism of purines in most of the somatic cells.

Just like allopurinol, referred to above, EHNA resembles purine base. Therefore, EHNA could also interfere with other enzymes of purine metabolism and this lack of specificity could lead to physiological disturbances.

Tests carried out with compounds of the invention in comparison with EHNA have shown that the indolizine derivatives of formula I exert a better specific action than EHNA.

All these properties taken together will render the indolizine derivatives of the invention extremely valuable as inhibitors with respect to adenosine deaminase. Thus, they could be widely used in immunopathology, for example, in the prevention of the rejection phenomenon in organ transplantations, in cases of auto-immune rheumatic disease such as chronic progressive polyarthritis and in cases of lupus erythematosus disseminatus, auto-immune glomerulonephritis, chronic severe hepatitis, disseminated sclerosis etc. . . .

Immunosuppression is not the only potential therapeutic application of substances exerting an inhibitory action with respect to adenosine deaminase. They could also exert a specific cytotoxic effect in lymphocytic neoplasia. Similarly, they could also potentiate the activity of anti-tumour and of antiviral agents such as 3'-deoxyadenosine i.e. cordycepine or adenine arabinoside.

"In vivo", adenine arabinoside (Ara-A) is rapidly converted by deamination to hypoxanthine arbinoside, a compound with less antiviral and anti-tumour activity than the parent compound.

Inhibition of this process by adenosine deaminase inhibitors leads to a potentiation of the antiviral and anti-tumour activity of adenine arabinoside.

Tests carried out "in vivo" have demonstrated that the compounds of the invention can act as inhibitors of the deamination of adenine arabinoside by adenosine deaminase thus leading to a synergic increase of the anti-herpetic activity of Ara-A in mice.

As inhibitors with respect to the action of adenosine deaminase, the following compounds may be regarded as some of the preferred derivatives of the invention:

1-Bromo-2-phenyl-3(3-bromo-4-hydroxy-benzoyl)-indolizine.

1-Bromo-2-(4-fluoro-phenyl)-3-(3-bromo-4-hydroxy-benzoyl)-indolizine.

1-Methoxy-2-phenyl-3-(3-bromo-4-hydroxy-benzoyl)-indolizine.

As already stated above, compounds of the invention have also been found to potentiate the cardiovascular effects of the catecholamines which will render these compounds useful in the treatment of, for example, disturbances of the cerebral vascular system.

At the cardiac level, this potentiation of the effects of the catecholamines results in an increase of the myocardial contractility which could be useful in the treatment of cardiac insufficiency and angina pectoris. In this connection, the following compound of formula I can be cited:

2-(4-Bromo-phenyl)-3-(3-bromo-4-hydroxy-benzoyl)-indolizine.

Trials have been performed in order to evaluate the pharmacological effects of the compounds of the invention.

Regarding the inhibitory effect with respect to the action of xanthine oxidase and of adenosine deaminase, trials were carried out "in vitro" in the absorption cell of a U.V. spectrophotometer. Tests "in vitro" were also undertaken regarding the uricosuric action and the inhibitory effect with respect to the action of adenosine deaminase.

I. Inhibition of the action of xanthine oxidase

This trial was performed with xanthine oxidase found in milk. The activity of the enzymatic preparation was measured by following the formation of uric acid starting from hypoxanthine in the presence of oxygen and of a phosphate buffer solution.

The experimental procedure described hereunder was used:

In the absorption cell, the following solutions were introduced:

1.5 ml of a 0.1 molar phosphate buffer solution (pH=7.4) saturated with oxygen.

0.3 ml of a 1 m molar solution of ethylene diamine tetraacetate.

0.8 ml of water.

0.01 ml of a commercial xanthine oxidase solution having a known concentration in enzyme.

0.01 ml of a $3.10^{-3}$ molar ethanolic solution of the compound to be tested.

The contents of the absorption cell were allowed to incubate for 2 minutes and then the enzymatic reaction was started by adding 0.3 ml of a $10^{-3}$ molar solution of hypoxanthine to the absorption cell. The reaction was followed by spectrophotometric recording of the oxidation rate of hypoxanthine at 293 nm and at 37° C. The optical density was automatically registered. The same measurements were performed with a control solution containing all the ingredients referred to above except the compound being tested.

In this way, a curve representing the variation in optical density in comparison with time was obtained with the solution containing the inhibitor on the one hand and devoid of inhibitor on the other. The slope of both curves was measured and expressed in the number of mols of uric acid formed in one minute. Thus, it was possible to compare the values obtained and calculate, in percent, the inhibition of the activity of xanthine oxidase provoked by a compound of the invention.

The following results were registered:

| R | $X_1$ | $X_2$ | $X_3$ | Inhibition of the action of xanthine oxidase in vitro (in %) at $10^{-5}$ M. |
|---|---|---|---|---|
| Methyl | H | H | Br | 74 |
| Isopropyl | H | H | Br | 94 |
| Ethyl | H | H | Cl | 87 |
| Isopropyl | H | H | Cl | 88 |
| Ethyl | H | H | OCH$_3$ | 57 |
| 4-Bromo-phenyl | H | H | Br | 22 |
| 3-Bromo-phenyl | H | H | Cl | 23 |
| Methyl | H | Br | Br | 91 |
| Ethyl | H | Br | Br | 98 |
| Isopropyl | H | Br | Br | 99 |
| 4-Bromo-phenyl | H | Br | Br | 23 |
| Methyl | H | Cl | Cl | 84 |
| Ethyl | H | Cl | Cl | 98 |
| Isopropyl | H | Cl | Cl | 96 |
| 4-Methyl-phenyl | Br | H | H | 48 |
| n-Propyl | Br | H | Cl | 84 |
| Ethyl | Br | Br | H | 93 |
| n-Propyl | Br | Br | H | 97 |
| 4-Methoxy-phenyl | Br | Br | H | 80 |
| n-Propyl | Br | Br | Br | 95 |
| Phenyl | Br | Br | Br | 48 |
| Methyl | Br | Cl | H | 44 |
| Ethyl | Cl | Br | H | 34 |
| Methyl | Br | Cl | Cl | 46 |
| Ethyl | Cl | Br | Br | 64 |

At a concentration of $10^{-6}$ M, 2-isopropyl-3-(3,5-dibromo-4-hydroxy-benzoyl)-indolizine already exerts 84% of inhibition of the action of xanthine oxidase "in vitro".

II. Uricosuric action

The uricosuric action was determined in humans after a single dose of 300 mg of 2-ethyl-3-(3,5-dibromo-4-hydroxy-benzoyl)-indolizine by oral route.

The urinary excretion of uric acid increased by 40% in the period between the 12th and the 24th hour after administration.

The mean increase in 24 hours was 22%.

The urinary volume for 24 hours was not greatly altered. On the other hand, uricemia was significantly lowered by 9% by the 5th hour at which time the compound under study was at its highest plasmatic level.

III. Inhibition of the action of adenosine deaminase

A. Test "in vitro"

This test was performed with adenosine deaminase obtained from calf intestine.

The experimental procedure described hereunder was used:

In the absorption cell the following solutions were introduced:

2.7 ml of a 0.1 molar phosphate buffer solution (pH=7.4)

0.3 ml of a $10^{-4}$ or $5.10^{-4}$ molar solution of adenosine in the phosphate buffer solution (final concentration in adenosine: $10^{-5}$ or $5.10^{-5}$ mol) 0.01 ml of a $3.10^{-3}$ molar ethanolic solution of the compound to be studied (about 10 milliunits)

The contents of the absorption cell were allowed to incubate for 2 minutes and then the enzymatic reaction was started by adding 0.03 ml of a commercial adenosine deaminase solution having a known concentration in enzyme. The reaction was performed at 30° C. and followed by spectrophotometric recording of the decrease in absorbance at 265 nm due to the transformation of adenosine into inosine by means of adenosine deaminase. This enzymatic reaction can be represented by the following equation:

Adenosine + $H_2O$ $\xrightarrow{\text{adenosine deaminase}}$ Inosine + $NH_3$

The same measurements were performed with a control solution containing all the ingredients referred to above except the compound being studied. Curves were then plotted representing the decrease in absorbance in comparison with time obtained on the one hand with the solution containing the inhibitor and on the other with the control solution.

The slope of both curves was measured and expressed in the number of mols of inosine formed in one minute. After that, the percent of inhibition of the activity of adenosine deaminase provoked by a compound of the invention was calculated.

The following results were registered:

| R | $X_1$ | $X_2$ | $X_3$ | Inhibition at $10^{-5}$ M adenosine | Inhibition at $5.10^{-5}$ M adenosine |
|---|---|---|---|---|---|
| n-Butyl | H | H | Br | 60 | — |
| n-Propyl | H | H | Cl | 42 | — |
| Phenyl | H | H | Br | 78 | — |
| 4-Fluoro-phenyl | H | H | Br | 60 | — |
| Phenyl | H | H | Cl | 58 | — |
| 3-Bromo-phenyl | Cl | H | H | — | 55 |
| Phenyl | Br | H | H | — | 52 |
| n-Butyl | Br | H | H | 45 | — |
| 4-Fluoro-phenyl | H | H | $OCH_3$ | — | 39 |
| Isopropyl | Br | Br | H | 75 | 54 |
| Phenyl | Br | Br | H | 100 | 88 |
| Isopropyl | H | Cl | Cl | — | 76 |
| Phenyl | Br | Cl | H | — | 86 |
| 4-Fluoro-phenyl | Br | Br | H | 100 | 94 |
| Phenyl | Cl | Cl | Cl | — | 57 |
| Isopropyl | Br | Br | Br | 57 | — |
| Phenyl | Br | Br | Br | 53 | 22 |
| Phenyl | $OCH_3$ | Cl | H | — | 82 |
| Phenyl | $OCH_3$ | Br | H | — | 91 |

Comparative trials undertaken with 2-ethyl-3-(4-hydroxy-benzoyl)-benzofuran and 2-phenyl-3-(3,5-dibromo-4-hydroxy-benzoyl)-benzofuran have shown that these compounds only attain 18%- and 15%-inhibition of adenosine deaminase at $10^{-5}$ M-adenosine respectively.

With regard to 2-ethyl-, 2-isopropyl- and 2-n-butyl-3-(3,5-dibromo-4-hydroxy-benzoyl)-benzofurans as well as 2-ethyl-3-(3,5-diiodo-4-hydroxy-benzoyl)-benzofuran, these compounds were found to be totally inactive with respect to the inhibition of adenosine deaminase at $10^{-5}$ M-adenosine.

At a concentration of $10^{-6}$ M, 1-bromo-2-phenyl- and 1-bromo-2-(4-fluorophenyl)-3-(3-bromo-4-hydroxy-benzoyl)-indolizines already exert 80% and 86% of inhibition of the action of adenosine deaminase "in vitro" respectively.

The inhibition of the action of adenosine deaminase by these two above-cited compounds has also been tested in intact cells by incubating ascites cells (Krebs II) in the presence of $^{14}C$ adenosine at a concentration of $5.10^{-5}$ M and by measuring the formation of inosine and hypoxanthine $^{14}C$. The deamination of adenosine due to the ascites cells was 50% inhibited in the presence of $2.10^{-6}$ M of 1-bromo-2-phenyl-3-(3-bromo-4-hydroxy-benzoyl)-indolizine and of $10^{-6}$ M of 1-bromo-2-(4-fluoro-phenyl)-3-(3-bromo-4-hydroxy-benzoyl)-indolizine.

B. Test "in vivo"

This test was carried out in order to determine the effects of adenine arabinoside (Ara-A) and compounds of the invention on the incidence of herpetic skin lesions and mortality of nu/nu mice inoculated with HSV-1 (KOS).

Figure 1:
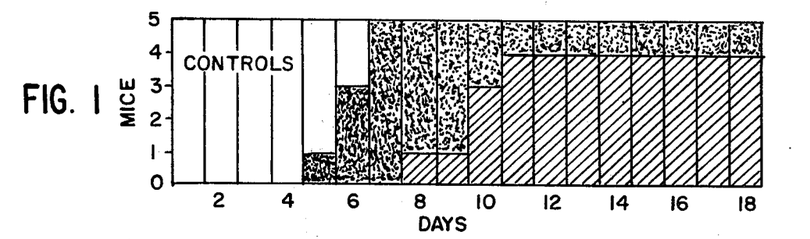
FIG. 1: represents the results obtained with controls having only received dimethylsulfoxide
Figure 2:
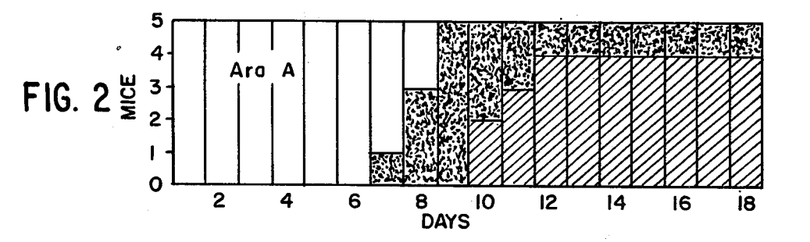
FIG. 2: represents the results obtained with Ara-A alone.
Figure 3:
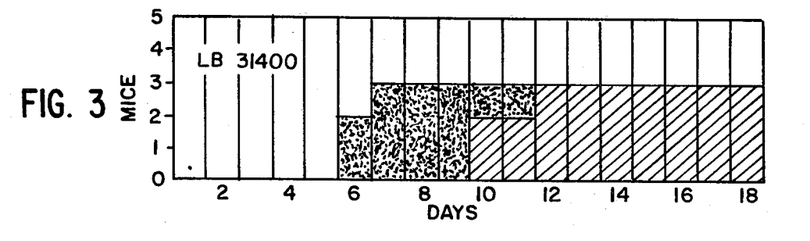
FIG. 3: represents the results obtained with 1-bromo-2-phenyl-3-(3-bromo-4-hydroxy-benzoyl)-indolizine referred to as LB 31400.
Figure 4:
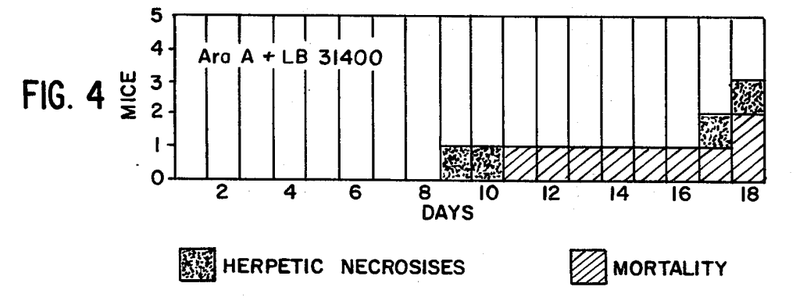
FIG. 4: represents the results obtained with Ara-A in association with LB 31400.

Athymic nude (nu/nu) mice, 20 to 25 days old, were inoculated intracutaneously with HSV-1 (KOS) at about $10^{4.5}$ PFU (plaque-forming units) per mouse. Ara-A and/or a compound of the invention were applied topically at 1% in dimethylsulfoxide, 4 times daily on days 0, 1, 2, 3 and 4. The number of mice with epidermal lesion (necrosis of at least 5 to 10 mm long) per total number of mice alive was registered.

The results are given in the attached drawing in which.

These results clearly show that the compound of the invention potentiates the antiviral activity of adenine arabinoside.

IV. Toxicity

Acute toxicity tests were performed in mice with compounds of the invention.

With 20 mg/kg of 1-bromo-2-phenyl- or 1-bromo-2-(4-fluoro-phenyl)-3-(3-bromo-4-hydroxy-benzoyl)-indolizine by intravenous route on death was registered after 14 days.

Administration of 1500 mg/kg of 1-bromo-2-isopropyl- or 2-ethyl-3-(3,5-dibromo-4-hydroxy-benzoyl)-indolizine by intragastric route gave the same result.

With regard to other possible properties of the compounds of the invention, particular attention may be drawn to the inhibitory action described above which these compounds exert on adenosine deaminase. As this action is also exerted by certain known compounds, for example coformycin and 2'-deoxycoformycin which possess antiparasitic properties, the compounds of the invention themselves may be endowed with antiparasitic properties which may prove to be extremely useful in the therapeutic treatment of a host.

It will be appreciated that for therapeutic use the compounds of the invention will normaly be administered in the form of a pharmaceutical or veterinary composition, which may be in a dosage unit form appropriate to the desired mode of administration.

Thus the pharmaceutical or veterinary composition may be in a dosage unit form suitable for oral administration, for example, a coated or uncoated tablet, a hard- or soft-gelatin capsule, a packaged powder, a suspension or a syrup. The composition may alternatively take the form of a suppository for rectal administration.

Irrespective of the form which the composition takes, the pharmaceutical or veterinary composition of the invention will normally be prepared by associating at least one of the compounds of formula I with an appropriate pharmaceutical carrier or excipient therefor, for example milk sugar, starches, talc, magnesium stearate, polyvinylpyrrolidone, alginic acid and colloidal silica.

The following Examples provide a non-limitative illustration of the process of preparing compounds of formula I and of a composition containing them:

EXAMPLE 1

2-Methyl-3-(3-bromo-4-hydroxy-benzoyl)-indolizine

To a solution of 101 g (0.73 mol) of 2-methyl-indolizine in 900 ml of dichlorethane were added, fairly quickly 284.5 g (0.73 mol) of 4-(3-bromo-tosyloxy)-benzoyl chloride in 900 ml of dichlorethane while the temperature was maintained between 40° and 50° C. The mixture was stirred for 20 hours and then evaporated to dryness. The residue so obtained was treated with 1 l of isopropanol for 2 hours under reflux to extract the impurities. After cooling under stirring, the medium was suction-filtered and washed with 1.5 l of isopropanol which provided 210 g of a crude crystalline product (yield: 59.4%)

The product so obtained was heated under reflux for 20 hours with 175 ml of a 30%-solution of sodium hydroxide in the presence of 175 ml of methanol. The medium was cooled, acidified with concentrated hydrochloric acid, suction-filtered, washed to neutrality and allowed to crystallize from dichlorethane.

In this manner, 98.8 g of 2-methyl-3-(3-bromo-4-hydroxy-benzoyl)-indolizine were obtained.

Yield: 80.3%

M.P.: 216°–217° C.

Following the same procedure as that described above but using the appropriate starting-products, the compounds listed hereunder were prepared:

| Compound | M.P. °C. |
| --- | --- |
| 2-Ethyl-3-(3-bromo-4-hydroxy-benzoyl)-indolizine | 210 (dichlorethane) |
| 2-n-Propyl-3-(3-bromo-4-hydroxy-benzoyl)-indolizine | 169 (dichlorethane) |
| 2-Isopropyl-3-(3-bromo-4-hydroxy-benzoyl)-indolizine | 89 (methanol) |
| 2-n-Butyl-3-(3-bromo-4-hydroxy-benzoyl)-indolizine | 167–168 (dichlorethane) |
| 2-Phenyl-3-(3-bromo-4-hydroxy-benzoyl)-indolizine | 219–220 (dioxan) |
| 2-(4-Methyl-phenyl)-3-(3-bromo-4-hydroxy-benzoyl)-indolizine | 212–213 (dichlorethane) |
| 2-(4-Fluoro-phenyl)-3-(3-bromo-4-hydroxy-benzoyl)-indolizine | 227 (dichlorethane) |
| 2-(4-Chloro-phenyl)-3-(3-bromo-4-hydroxy-benzoyl)-indolizine | 240–241 (dioxan) |
| 2-(4-Bromo-phenyl)-3-(3-bromo-4-hydroxy-benzoyl)-indolizine | 235–236 (dichlorethane) |
| 2-(3-Bromo-phenyl)-3-(3-bromo-4-hydroxy-benzoyl)-indolizine | 199–200 (dichlorethane) |
| 2-(3,4-Dichloro-phenyl)-3-(3-bromo-4-hydroxy-benzoyl)-indolizine | 251 (dioxan) |

EXAMPLE 2

2-n-Propyl-3-(3-chloro-4-hydroxy-benzoyl)-indolizine

To a solution of 3.2 g (0.02 mol) of 2-n-propyl-indolizine in 20 ml of dichlorethane, were added at room-temperature, 8 g (0.02 mol) of 4-(3-chloro-tosyloxy)-benzoyl chloride in 80 ml of dichlorethane. The mixture was stirred for 20 hours and then evaporated to dryness. In this way, 9.4 g of an oily product were obtained which were refluxed for 4 hours with 50 ml of a 30%-sodium hydroxyde solution in the presence of 50 ml of methanol. After cooling, the medium was acidified with concentrated hydrochloric acid, suction-filtered, washed to neutrality and recrystallized from 10 ml of methanol. In this manner, 1 g of 2-n-propyl-3-(3-chloro-4-hydroxy-benzoyl)-indolizine was obtained.

Yield: 15.9%

M.P.: 165° C.

Following the same procedure as that described above but using the appropriate starting-products, the compounds listed hereunder were prepared:

| Compound | M.P. °C. |
|---|---|
| 2-Methyl-3-(3-chloro-4-hydroxy-benzoyl)-indolizine | 239–240 (dioxan) |
| 2-Ethyl-3-(3-chloro-4-hydroxy-benzoyl)-indolizine | 208–209 (dioxan) |
| 2-Isopropyl-3-(3-chloro-4-hydroxy-benzoyl)-indolizine | 161–162 (methanol) |
| 2-n-Butyl-3-(3-chloro-4-hydroxy-benzoyl)-indolizine | 151–152 (benzene) |
| 2-Phenyl-3-(3-chloro-4-hydroxy-benzoyl)-indolizine | 210–211 (dichlorethane) |
| 2-(4-Methyl-phenyl)-3-(3-chloro-4-hydroxy-benzoyl)-indolizine | 215–216 (dioxan) |
| 2-(3-Bromo-phenyl)-3-(3-chloro-4-hydroxy-benzoyl)-indolizine | 181–182 (dichlorethane) |
| 2-(4-Chloro-phenyl)-3-(3-chloro-4-hydroxy-benzoyl)-indolizine | 240–241 (dioxan) |
| 2-(4-Bromo-phenyl)-3-(3-chloro-4-hydroxy-benzoyl)-indolizine | 232–233 (dioxan) |

EXAMPLE 3

1-Methoxy-2-phenyl-3-(3-bromo-4-hydroxy-benzoyl)-indolizine

To a solution of 19.4 g (0.09 mol) of 1-methoxy-2-phenyl-indolizine in 100 ml of dichlorethane, were added, at room-temperature, 33.9 g (0.09 mol) of 4-(3-bromo-tosyloxy)-benzoyl chloride in 100 ml of dichlorethane. The mixture was stirred for 20 hours and then evaporated to dryness. In this way, a crystalline product was obtained which was recrystallized from 250 ml of isopropanol giving 25.4 g of a pure product (M.P.: 153° C.).

The product so obtained was refluxed for 4 hours with 100 ml of a 30%-sodium hydroxide solution in the presence of 50 ml of methanol. After cooling, the medium was acidified with concentrated hydrochloric acid, suction-filtered, washed to neutrality and recrystallized from a 1/1 methanol/chloroform mixture.

In this manner, 14.6 g of 1-methoxy-2-phenyl-3-(3-bromo-4-hydroxy-benzoyl)-indolizine were obtained.

Yield: 78.5%

M.P.: 205° C.

Following the same procedure as that described above but using the appropriate starting-products, the compounds listed hereunder were prepared:

| Compound | M.P. °C. |
|---|---|
| 1-Methoxy-2-phenyl-3-(4-hydroxy-benzoyl)-indolizine | 199 (methanol) |
| 1-Methoxy-2-phenyl-3-(3-chloro-4-hydroxy-benzoyl)-indolizine | 203 (isopropanol) |
| 1-Methoxy-2-phenyl-3-(3-methoxy-4-hydroxy-benzoyl)-indolizine | 180 (methanol) |
| 2-Methyl-3-(3-methoxy-4-hydroxy-benzoyl)-indolizine | 182 (isopropanol) |
| 2-Ethyl-2-(3-methoxy-4-hydroxy-benzoyl)-indolizine | 157 (isopropanol) |
| 2-(4-Fluoro-phenyl)-3-(3-methoxy-4-hydroxy-benzoyl)-indolizine | 166 (benzene) |
| 1-Bromo-2-methyl-3-(3-methoxy-4-hydroxy-benzoyl)-indolizine | 155 (methanol) |
| 1-Bromo-2-ethyl-3-(3-methoxy-4-hydroxy-benzoyl)-indolizine | 160 (methanol) |

EXAMPLE 4

2-Ethyl-3-(3,5-dibromo-4-hydroxy-benzoyl)-indolizine

To a solution of 78.8 g (0.54 mol) of 2-ethyl-indolizine in 1500 ml of dichlorethane, 180 g (0.57 mol) of 3,5-dibromo-4-hydroxy-benzoyl chloride (M.P. 98°–100° C.), were added rapidly. The mixture was stirred for 24 h at room-temperature and then allowed to stand for 24 hours. The product so formed was filtered and washed on the filter with dichlorethane and then with ethanol until a yellow filtrate appeared.

In this way, 112.1 g of a yellow crystalline solid were obtained which when recrystallized from 2000 ml of dichlorethane provided 84 g of the desired product. M.P.: 213° C.

A second amount of the desired compound was obtained by concentrating the filtrate and the mother-liquors to about 500 ml.

After being allowed to stand, the product was treated on the filter as described above. In this way, 26 g of crude product were obtained which after recrystallization from dichlorethane gave 23.9 g of the desired product.

In this manner, 107.9 g of 2-ethyl-3-(3,5-dibromo-4-hydroxy-benzoyl)-indolizine were obtained.

Yield: 47.2%

M.P.: 213° C.

Using the same procedure as that described above, the compounds hereunder were prepared starting from the appropriate products:

| Compound | M.P. °C. |
|---|---|
| 2-Methyl-3-(3,5-dibromo-4-hydroxy benzoyl)-indolizine | 210 (ethanol) |
| 2-n-Propyl-3-(3,5-dibromo-4-hydroxy-benzoyl)-indolizine | 143 (isopropanol/water) |
| 2-Isopropyl-3-(3,5-dibromo-4-hydroxy-benzoyl)-indolizine | 198 (ethanol) |
| 2-n-Butyl-3-(3,5-dibromo-4-hydroxy-benzoyl)-indolizine | 171 (ethanol) |
| 2-Phenyl-3-(3,5-dibromo-4-hydroxy-benzoyl)-indolizine | 189 (ethanol/water) |
| 2-(4-Methyl-phenyl)-3-(3,5-dibromo-4-hydroxy-benzoyl)-indolizine.Sodium salt | 255(pasty) (water) |
| 2-(4-Methoxy-phenyl)-3-(3,5-dibromo-4-hydroxy-benzoyl)-indolizine | 192 (isopropanol/water) |
| 2-(4-Fluoro-phenyl)-3-(3,5-dibromo-4-hydroxy-benzoyl)-indolizine.Sodium salt | 250(pasty) (water) |
| 2-(4-Chloro-phenyl)-3-(3,5-dibromo-4-hydroxy-benzoyl)-indolizine | 139 (heptane/benzene) |
| 2-(3,4-Dichloro-phenyl)-3-(3,5-dibromo-4-hydroxy-benzoyl)-indolizine | 186 (heptane/benzene) |
| 2-(2-Bromo-phenyl)-3-(3,5-dibromo-4-hydroxy-benzoyl)-indolizine | 200 (heptane/benzene) |
| 2-(3-Bromo-phenyl)-3-(3,5-dibromo-4-hydroxy-benzoyl)-indolizine | 210 (heptane/benzene) |
| 2-(4-Bromo-phenyl)-3-(3,5-dibromo-4-hydroxy-benzoyl)-indolizine | 164 (heptane/benzene) |

EXAMPLE 5

2-Ethyl-3-(3,5-dichloro-4-hydroxy-benzoyl)-indolizine

To a solution of 10 g (0.068 mol) of 2-ethyl-indolizine in 250 ml of dichlorethane, 15.8 g (0.07 mol) of 3,5-dichloro-4-hydroxy-benzoyl chloride (M.P.: 92° C.) were added rapidly. The mixture was stirred for 24 hours at room-temperature and the solvent was then eliminated under reduced pressure. The product so obtained was purified by elution chromatography on silica, the eluent being chloroform.

In this manner, 11.5 g of a yellow solid were obtained which when recrystallized from 300 ml of dichlorethane gave 8.4 g of 2-ethyl-3-(3,5-dichloro-4-hydroxy-benzoyl)-indolizine.

Yield: 37%

M.P.: 206° C.

Using the same procedure as that described above but starting from the appropriate products, the compounds listed hereunder were prepared:

| Compound | M.P. °C. |
| --- | --- |
| 2-Methyl-3-(3,5-dichloro-4-hydroxy-benzoyl)-indolizine | 190 (dichlorethane/heptane 80-20) |
| 2-n-Propyl-3-(3,5-dichloro-4-hydroxy-benzoyl)-indolizine | 140 (dichlorethane/heptane 70-30) |
| 2-Isopropyl-3-(3,5-dichloro-4-hydroxy-benzoyl)-indolizine | 200 (dichlorethane) |
| 2-Phenyl-3-(3,5-dichloro-4-hydroxy-benzoyl)-indolizine | 193 (isopropanol) |
| 2-(4-Bromo-phenyl)-3-(3,5-dichloro-4-hydroxy-benzoyl)-indolizine | 202 (isopropanol) |

EXAMPLE 6

1-Bromo-2-ethyl-3-(4-hydroxy-benzoyl)-indolizine

To a mixture of 5.3 g (0.02 mol) of 2-ethyl-3-(4-hydroxy-benzoyl)-indolizine, 5.6 g (0.041 mol) of sodium acetate trihydrate and 50 ml of acetic acid there were added drop-by-drop in 3 h ¾ 3.25 g (0.021 mol) of bromine in 50 ml of acetic acid. During this operation, the temperature was maintained between 20° and 22° C. Stirring was continued for ¾ hour and 150 ml of water were then added. The mixture was stirred for a further hour and the precipitate so formed was suction-filtered. This precipitate was converted to paste form in 50 ml and then in 100 ml of benzene which gave 6.35 g of a solid. This solid was then recrystallized from 90 ml of methanol.

In this manner, 4.4 g of 1-bromo-2-ethyl-3-(4-hydroxy-benzoyl)-indolizine were obtained.

Yield: 63.9%

M.P.: 160°-161.5° C.

Using the same procedure as that described above but starting from the appropriate products, the compounds listed hereunder were prepared:

| Compound | M.P. °C. |
| --- | --- |
| 1-Bromo-2-methyl-3-(4-hydroxy-benzoyl)-indolizine | 238-239 (dichlorethane) |
| 1-Bromo-2-n-butyl-3-(4-hydroxy-benzoyl)-indolizine | 160-162 (benzene) |
| 1-Bromo-2-n-pentyl-3-(4-hydroxy-benzoyl)-indolizine | 155-157 (dichlorethane) |
| 1-Bromo-2-n-hexyl-3-(4-hydroxy-benzoyl)-indolizine | 162-163 (dichlorethane) |
| 1-Bromo-2-n-heptyl-3-(4-hydroxy-benzoyl)-indolizine | 145-149 (benzene) |
| 1-Bromo-2-n-octyl-3-(4-hydroxy-benzoyl)-indolizine | 132-133 (dichorethane) |
| 1-Bromo-2-phenyl-3-(4-hydroxy-benzoyl)-indolizine | 210 (dioxan) |
| 1-Bromo-2-(4-methyl-phenyl)-3-(4-hydroxy-benzoyl)-indolizine | 197-198 (dichlorethane) |
| 1-Bromo-2-(4-bromo-phenyl)-3-(4-hydroxy-benzoyl)-indolizine | 220-225 (benzene) |
| 1-Bromo-2-(3-bromo-phenyl)-3-(4-hydroxy-benzoyl)-indolizine | 225 (carbon tetrachloride) |
| 1-Bromo-2-(3-chloro-4-methyl-phenyl)-3-(4-hydroxy-benzoyl)-indolizine | 210 (benzene) |
| 1-Bromo-2-(3,4-dichloro-phenyl)-3-(4-hydroxy-benzoyl)-indolizine | 240 (dichlorethane) |

EXAMPLE 7

1-Chloro-2-ethyl-3-(4-hydroxy-benzoyl)-indolizine

To a solution of 50.4 g (0.12 mol) of 2-ethyl-3-(4-tosyloxy-benzoyl)-indolizine in 1100 ml of dichlorethane, 26.8 g (0.2 mol) of N-chlorosuccinimide were added by fractions in 2 hours.

During this operation, the temperature was maintained between 0° and 10° C. The dichloroethane solution was stirred for one hour and washed with 500 ml of water. The solvent was distilled under vacuum and the residue was allowed to crystallize from 500 ml of methanol.

In this way, 20.65 g of a product were obtained which was heated under reflux for 4 hours in the presence of 45 ml of water, 5.4 g of sodium hydroxide and 50 ml of isopropanol.

The medium was cooled to 20° C., acidified by adding 10 ml of concentrated hydrochloric acid and stirred for about 12 hours.

The precipitate so formed was suction-filtered, thus providing 12.7 g of the desired product which were recrystallized from 400 ml of methanol. In this manner, 10.8 g of 1-chloro-2-ethyl-3-(4-hydroxy-benzoyl)-indolizine were obtained.

Yield: 30%

M.P.: 179° C.

Following the same procedure as that described above but using the appropriate starting-compounds, the products hereunder were prepared:

| Compound | M.P. °C. |
| --- | --- |
| 1-Chloro-2-methyl-3-(4-hydroxy-benzoyl)-indolizine | 212 |
| 1-Chloro-2-n-propyl-3-(4-hydroxy-benzoyl)-indolizine | 165 (benzene/cyclohexane 1/1) |
| 1-Chloro-2-n-butyl-3-(4-hydroxy-benzoyl)-indolizine | 156 (benzene) |
| 1-Chloro-2-(3-bromo-phenyl)-3-(4-hydroxy-benzoyl)indolizine | 201-202 (isopropanol) |
| 1-Chloro-2-(4-chloro-phenyl)-3-(4-hydroxy-benzoyl)-indolizine | 249-250 (dioxan) |
| 1-Chloro-2-(4-bromo-phenyl)-3-(4-hydroxy-benzoyl)indolizine | 237-238 (dioxan) |

EXAMPLE 8

1-Bromo-2-ethyl-3-(3-bromo-4-hydroxy-benzoyl)-indolizine

To a mixture of 1.3 g (0.004 mol) of 2-ethyl-3-(3-bromo-4-hydroxy-benzoyl)-indolizine, 0.6 g (0.09 mol) of anhydrous sodium acetate and 10 ml of acetic acid, there was added, drop-by-drop in 3 h ¾ while stirring, 0.6 g (0.004 mol) of bromine in 10 ml of acetic acid. During this operation, the temperature was maintained between 20° and 22° C. The medium was stirred for a further 45 minutes and then poured into 50 ml of water.

The precipitate so formed was suction-filtered and washed to neutrality. In this way, 1.4 g of a solid was obtained which when recrystallized from 20 ml of chloroform gave 0.7 g of 1-bromo-2-ethyl-3-(3-bromo-4-hydroxy-benzoyl)-indolizine.

Yield: 45%
M.P.: 213°–214° C.

Following the same procedure as that described above but using the appropriate starting-products, the compounds listed hereunder were prepared:

| Compound | M.P. °C. |
|---|---|
| 1-Bromo-2-methyl-3-(3-bromo-4-hydroxy-benzoyl)-indolizine | 245–246 (dichlorethane) |
| 1-Bromo-2-n-propyl-3-(3-bromo-4-hydroxy-benzoyl)-indolizine | 189–191 (benzene) |
| 1-Bromo-2-isopropyl-3-(3-bromo-4-hydroxy-benzoyl)-indolizine | 130–132 (benzene) |
| 1-Bromo-2-n-butyl-3-(3-bromo-4-hydroxy-benzoyl)-indolizine | 183–184 (benzene) |
| 1-Bromo-2-n-pentyl-3-(3-bromo-4-hydroxy-benzoyl)-indolizine | 174–175 (dichlorethane) |
| 1-Bromo-2-n-hexyl-3-(3-bromo-4-hydroxy-benzoyl)indolizine | 175–177 (dichlorethane) |
| 1-Bromo-2-n-heptyl-3-(3-bromo-4-hydroxy-benzoyl)-indolizine | 165–166 (dichlorethane) |
| 1-Bromo-2-n-octyl-3-(3-bromo-4-hydroxy-benzoyl)-indolizine | 161.5–163 (dichlorethane) |
| 1-Bromo-2-phenyl-3-(3-bromo-4-hydroxy-benzoyl)-indolizine | 184.5–186 (benzene) |
| 1-Bromo-2-(4-methyl-phenyl)-3-(3-bromo-4-hydroxy-benzoyl)-indolizine | 231 (dichlorethane) |
| 1-Bromo-2-(4-methoxy-phenyl)-3-(3-bromo-4-hydroxy-benzoyl)-indolizine | 204–205 (dichlorethane) |
| 1-Bromo-2-(4-fluoro-phenyl)-3-(3-bromo-4-hydroxy-benzoyl)-indolizine | 196 (benzene) |
| 1-Bromo-2-(4-chloro-phenyl)-3-(3-bromo-4-hydroxy-benzoyl)-indolizine | 228–230 (benzene) |
| 1-Bromo-2-(4-bromo-phenyl)-3-(3-bromo-4-hydroxy-benzoyl)-indolizine | 240–245 (dichlorethane) |
| 1-Bromo-2-(3-bromo-phenyl)-3-(3-bromo-4-hydroxy-benzoyl)-indolizine | 185–186 (carbon tetrachloride) |
| 1-Bromo-2-(2-bromo-phenyl)-3-(3-bromo-4-hydroxy-benzoyl)-indolizine | 213–214 (benzene) |
| 1-Bromo-2-(3-chloro-4-methyl-phenyl)-3-(3-bromo-4-hydroxy-benzoyl)-indolizine | 201–202 (dichlorethane) |
| 1-Bromo-2-(3,4-dichloro-phenyl)-3-(3-bromo-4-hydroxy-benzoyl)-indolizine | 207–209 (benzene) |
| 1-Bromo-2-methyl-3-(3-chloro-4-hydroxy-benzoyl)-indolizine | 228 (dioxan) |
| 1-Bromo-2-ethyl-3-(3-chloro-4-hydroxy-benzoyl)-indolizine | 191–192 (dichlorethane) |
| 1-Bromo-2-n-propyl-3-(3-chloro-4-hydroxy-benzoyl)-indolizine | 180–181 (isopropanol) |
| 1-Bromo-2-isopropyl-3-(3-chloro-4-hydroxy-benzoyl)-indolizine | 174 (benzene) |
| 1-Bromo-2-n-butyl-3-(3-chloro-4-hydroxy-benzoyl)-indolizine | 177–178 (dichlorethane) |
| 1-Bromo-2-phenyl-3-(3-chloro-4-hydroxy-benzoyl)-indolizine | 198–199 (benzene) |
| 1-Bromo-2-(4-chloro-phenyl)-3-(3-chloro-4-hydroxy-benzoyl)-indolizine | 212–213 (dichlorethane) |
| 1-Bromo-2-(3-bromo-phenyl)-3-(3-chloro-4-hydroxy-benzoyl)-indolizine | 126–128 (benzene) |
| 1-Bromo-2-(4-bromo-phenyl)-3-(3-chloro-4-hydroxy-benzoyl)-indolizine | 231–232 (dichlorethane) |

EXAMPLE 9

1-Chloro-2-ethyl-3-(3-bromo-4-hydroxy-benzoyl)-indolizine

To a solution of 4.98 g (0.01 mol) of 2-ethyl-3-(3-bromo-4-tosyloxybenzoyl)-indolizine in 100 ml of dichlorethane, were added, by small fractions and under vigorous stirring, 1.98 g (0.015 mol) of N-chlorosuccinimide. The temperature was maintained between 19° and 22° C. during the operation of introduction. The medium was stirred at room-temperature for 2 hours and then the solvent was eliminated under reduced pressure.

To the crude prouct so obtained, 50 ml of acetone and 100 ml of methanol were added and the medium was stirred for 1 hour so as to solubilize the impurities formed.

After suction-filtering and washing with methanol 2.05 g of the product were obtained (yield: 38.5%) which were heated under reflux for 20 hours with a solution of 10 ml of 30% -sodium hydroxide in the presence of 10 ml of methanol. After cooling, the medium was acidified with concentrated hydrochloric acid, suction-filtered and washed to neutrality.

In this manner, 0.97 g of 1-chloro-2-ethyl-3-(3-bromo-4-hydroxy-benzoyl)-indolizine was obtained.
Yield: 66.9%
M.P.: 204° C.

Following the same procedure as that described above but using the appropriate starting-products, the compounds hereunder were prepared:

| Compound | M.P. °C. |
|---|---|
| 1-Chloro-2-ethyl-3-(3-chloro-4-hydroxy-benzoyl)-indolizine | 183–184 (benzene) |
| 1-Chloro-2-isopropyl-3-(3-chloro-4-hydroxy-benzoyl)-indolizine | ±93 |
| 1-Chloro-2-phenyl-3-(3-chloro-4-hydroxy-benzoyl)-indolizine | 192–193 (isopropanol) |
| 1-Chloro-2-(3-bromo-phenyl)-3-(3-chloro-4-hydroxy-benzoyl)-indolizine | 157.5–158.5 (ethyl acetate) |

EXAMPLE 10

1-Bromo-2-ethyl-3-(3,5-dibromo-4-hydroxy-benzoyl)-indolizine

To a solution of 4.2 g (0.01 mol) of 2-ethyl-3-(3,5-dibromo-4-hydroxy-benzoyl)-indolizine in 100 ml of dioxan, were added 1.6 g (0.02 mol) of anhydrous sodium acetate. Under vigorous stirring, a solution of 1.6 g (0.01 mol) of bromine in 20 ml of dioxan was added drop-by-drop. The temperature was maintained between 20° and 22° C. during the operation of introduction. After the medium was stirred for a further hour, the reaction product was poured into 250 ml of water. A yellow-green precipitate formed which was filtered out and washed with water to neutrality of the filtrate.

After drying under vacuum, 5.2 g of a crude product were obtained which were recrystallized from 50 ml of dichloroethane.

In this manner, 4.2 g of 1-bromo-2-ethyl-3-(3,5-dibromo-4-hydroxy-benzoyl)-indolizine were obtained after treatment with active charcoal.
Yield: 83.6%
M.P.: 195° C.

Following the same procedure as that described above but using the appropriate starting-products, the compounds listed hereunder were prepared:

| Compound | M.P. °C. |
|---|---|
| 1-Bromo-2-methyl-3-(3,5-dibromo-4-hydroxy-benzoyl)-indolizine | 254–255 (dichlorethane) |
| 1-Bromo-2-n-propyl-3-(3,5-dibromo-4-hydroxy-benzoyl)-indolizine | 183–184 (benzene) |
| 1-Bromo-2-isopropyl-3-(3,5-dibromo-4-hydroxy-benzoyl)-indolizine | 188–189 (carbon tetrachloride) |

-continued

| Compound | M.P. °C. |
| --- | --- |
| 1-Bromo-2-n-butyl-3-(3,5-dibromo-4-hydroxy-benzoyl)-indolizine | 162–163 (heptane) |
| 1-Bromo-2-n-pentyl-3-(3,5-dibromo-4-hydroxy-benzoyl)-indolizine | 139–140 (carbon tetrachloride) |
| 1-Bromo-2-n-hexyl-3-(3,5-dibromo-4-hydroxy-benzoyl)-indolizine | 152–153 (benzene) |
| 1-Bromo-2-n-heptyl-3-(3,5-dibromo-4-hydroxy-benzoyl)-indolizine | 167–168 (benzene) |
| 1-Bromo-2-n-octyl-3-(3,5-dibromo-4-hydroxy-benzoyl)-indolizine | 153–154 (benzene) |
| 1-Bromo-2-phenyl-3-(3,5-dibromo-4-hydroxy-benzoyl)-indolizine | 211–212 (benzene) |
| 1-Bromo-2-(4-methyl-phenyl)-3-(3,5-dibromo-4-hydroxy-benzoyl)-indolizine | 148–150 (cyclohexane/carbon tetrachloride) |
| 1-Bromo-2-(4-methoxy-phenyl)-3-(3,5-dibromo-4-hydroxy-benzoyl)-indolizine | 167–168 (isopropanol) |
| 1-Bromo-2-(4-fluoro-phenyl)-3-(3,5-dibromo-4-hydroxy-benzoyl)-indolizine | 191–192 (benzene) |
| 1-Bromo-2-(4-chloro-phenyl)-3-(3,5-dibromo-4-hydroxy-benzoyl)-indolizine | 203–204 (carbon tetrachloride) |
| 1-Bromo-2-(4-bromo-phenyl)-3-(3,5-dibromo-4-hydroxy-benzoyl)-indolizine | 203–204 (carbon tetrachloride) |
| 1-Bromo-2-(3-bromo-phenyl)-3-(3,5-dibromo-4-hydroxy-benzoyl)-indolizine | 269–270 (dichlorethane) |
| 1-Bromo-2-(2-bromo-phenyl)-3-(3,5-dibromo-4-hydroxy-benzoyl)-indolizine | 176–177 (carbon tetrachloride) |
| 1-Bromo-2-(3-chloro-4-methyl-phenyl)-3-(3,5-dibromo-4-hydroxy-benzoyl)-indolizine | 214–215.5 (dichlorethane) |
| 1-Bromo-2-(3,4-dichloro-phenyl)-3-(3,5-dibromo-4-hydroxy-benzoyl)-indolizine | 244 (benzene) |

EXAMPLE 11

1-Bromo-2-ethyl-3-(3,5-dibromo-4-hydroxy-benzoyl)-indolizine

To a mixture of 5.3 g (0.02 mol) of 2-ethyl-3-(4-hydroxy-benzoyl)-indolizine, 17.7 g (0.13 mol) of sodium acetate trihydrate and 50 ml of acetic acid there were added, drop-by-drop in 3h, 10.55 g (0.066 mol) of bromine in 50 ml of acetic acid. During this operation, the temperature was maintained between 20° and 22° C. Stirring was maintained for 18 hours. After that, the precipitate was suction-filtered and washed with acetic acid and water. To the filtrate, 450 ml of water were added and the medium was again filtered. The two precipitates were collected and recrystallized from carbon tetrachloride.

In this manner, 7.9 g of 1-bromo-2-ethyl-3-(3,5-dibromo-4-hydroxy-benzoyl)-indolizine were obtained. Yield: 79%.

EXAMPLE 12

1-Chloro-2-ethyl-3-(3,5-dibromo-4-hydroxy-benzoyl)-indolizine

To a solution of 4.2 g (0.01 mol) of 2-ethyl-3-(3,5-dibromo-4-hydroxy-benzoyl)-indolizine in 300 ml of dichlorethane, were added, by small fractions and while stirring, 1.8 g (0.015 mol) of N-chlorosuccinimide. The temperature was maintained between 15° and 20° C. during the operation of introduction. The medium was stirred for 24 hours at room-temperature and the solvent was then eliminated under reduced pressure. The crude product so obtained was purified by elution chromatography on silica, the eluent being chloroform.

In this manner, 2.3 g of 1-chloro-2-ethyl-3-(3,5-dibromo-4-hydroxy-benzoyl)-indolizine were obtained after recrystallization from a 70/30 mixture of dichlorethane/heptane.

Yield: 50%

M.P.: 194° C.

Following the same procedure as that described above, but using the appropriate starting-products, the compounds hereunder were prepared:

| Compound | M.P. °C. |
| --- | --- |
| 1-Chloro-2-phenyl-3-(3,5-dibromo-4-hydroxy-benzoyl)-indolizine | 207 (heptane/dichlorethane 30/70) |
| 1-Chloro-2-isopropyl-3-(3-bromo-4-hydroxy-5-chloro-benzoyl)-indolizine | 192–193 (dichlorethane) |
| 1-Chloro-2-ethyl-3-(3,5-dichloro-4-hydroxy-benzoyl)-indolizine | 145 (heptane/dichlorethane 50/50) |
| 1-Chloro-2-phenyl-3-(3,5-dichloro-4-hydroxy-benzoyl)-indolizine | 228 (isopropanol) |

EXAMPLE 13

1-Bromo-2-methyl-3-(3,5-dichloro-4-hydroxy-benzoyl)-indolizine

To a solution of 3.2 g (0.01 mol) of 2-methyl-3-(3,5-dichloro-4-hydroxy-benzoyl)-indolizine in 100 ml of dioxan, were added 1.6 g (0.02 mol) of anhydrous sodium acetate. Under vigorous stirring, 1.6 g (0.01 mol) of bromine were added drop-by-drop at 20° C. The temperature was maintained between 20° and 22° C. during the operation of introduction.

After the mixture had been stirred for a further hour, the reaction product was poured into 250 ml of water. A yellow-green precipitate formed which was filtered out and washed with water to neutrality of the filtrate. After drying under vacuum, a crude product was obtained which was recrystallized from dichlorethane/heptane 80/20.

In this manner, 1.7 g of 1-bromo-2-methyl-3-(3,5-dichloro-4-hydroxy-benzoyl)-indolizine was obtained after treatment with active charcoal.

Yield: 42.6%

M.P.: 240° C.

Following the same procedure as that described above but using the appropriate starting-products, the compounds hereunder were prepared:

| Compound | M.P. °C. |
| --- | --- |
| 1-Bromo-2-ethyl-3-(3,5-dichloro-4-hydroxy-benzoyl)-indolizine | 174 (dichlorethane/heptane 90/10) |
| 1-Bromo-2-phenyl-3-(3,5-dichloro-4-hydroxy-benzoyl)-indolizine | 236 (dichlorethane/heptane 90/10) |

EXAMPLE 14

A pharmaceutical unit for oral administration was prepared by introducing by known techniques 300 mg of 2-ethyl-3-(3,5-dibromo-4-hydroxy-benzoyl)-indolizine into a soft-gelatin capsule.

We claim:

1. An indolizine derivative of the formula:

wherein R represents a straight- or branched-chain alkyl radical having from 1 to 8 carbon atoms, or a phenyl group non-substituted or bearing one or two substituents, which may be the same or different, selected from fluorine, chlorine and bromine and from lower alkyl and alkoxy groups, $X_1$ represents chlorine, bromine or methoxy, and $X_2$ and $X_3$, which may be the same or different, each represent hydrogen, chlorine, bromine or methoxy.

2. An indolizine derivative according to claim 1 wherein R represents a straight- or branched-chain alkyl radical having from 1 to 8 carbon atoms, a phenyl radical, a mono-fluoro-, mono-chloro, mono-bromo-, mono-methyl- or mono-methoxy-substituted-phenyl radical, a di-fluoro-, di-chloro, di-bromo-substituted-phenyl radical or a methyl-phenyl radical substituted in the aromatic moiety by an atom of fluorine, chlorine or bromine, $X_1$ represents chlorine, bromine or methoxy, and $X_2$ and $X_3$, which may be the same or different, each represent hydrogen, chlorine, bromine or methoxy.

3. 1-Bromo-2-n-propyl-3-(3,5-dibromo-4-hydroxy-benzoyl)-indolizine.

4. 1-Bromo-2-phenyl-3-(3-bromo-4-hydroxy-benzoyl)-indolizine.

5. 1-Bromo-2-(4-fluoro-phenyl)-3-(3-bromo-4-hydroxy-benzoyl)-indolizine.

6. 1-Methoxy-2-phenyl-3-(3-bromo-4-hydroxy-benzoyl)-indolizine.

7. A pharmaceutical or veterinary composition for treating physiological disturbances consequent upon an excess of uric acid and consequent upon disorders of the immunization system containing, as active principle, at least one indolizine derivative according to claim 1 or 2, in association with a pharmaceutical carrier or excipient therefor, in daily dosage of about 300 mg per 60 kg of body weight.

8. A pharmaceutical or veterinary composition for treating physiological disturbances consequent upon an excess of uric acid and consequent upon disorders of the immunization system containing as active ingredient at least one indolizine derivative according to any one of claims 3, 4, 5 or 6, in association with a pharmaceutical carrier or excipient therefor, in daily dosage of about 300 mg per 60 kg of body weight.

9. A method of treating physiological disturbances consequent upon disorders of the immunization system in a host in need of such treatment, which method comprises administering to said host an effective dose of at least one indolizine derivative according to claim 1 or 2.

* * * * *